(12) United States Patent
Baca et al.

(10) Patent No.: US 6,919,019 B2
(45) Date of Patent: Jul. 19, 2005

(54) LASER WATER DETECTION, TREATMENT AND NOTIFICATION SYSTEMS AND METHODS

(75) Inventors: Anthony Michael Baca, Albuquerque, NM (US); Luis M. Ortiz, Sante Fe, NM (US); Thomas A. Crow, Albuquerque, NM (US); Donald W. Wichers, Albuquerque, NM (US)

(73) Assignee: Saltech Corporation, Albuquerque, NM (US)

( * ) Notice: Subject to any disclaimer, the term of this patent is extended or adjusted under 35 U.S.C. 154(b) by 0 days.

(21) Appl. No.: 10/389,355

(22) Filed: Mar. 13, 2003

(65) Prior Publication Data

US 2004/0020862 A1 Feb. 5, 2004

Related U.S. Application Data

(60) Provisional application No. 60/364,509, filed on Mar. 14, 2002.

(51) Int. Cl.⁷ .................................................. C02F 1/32
(52) U.S. Cl. .................. 210/97; 210/198.1; 422/186.3; 422/62; 250/437
(58) Field of Search ............................... 210/739, 748, 210/764, 87, 97, 198.1, 205; 422/24, 186.3, 62; 250/432 R, 435, 436, 437; 73/61.41–61.79

(56) References Cited

U.S. PATENT DOCUMENTS

| | | | | |
|---|---|---|---|---|
| 4,372,860 A | * | 2/1983 | Kaas | 210/748 |
| 4,661,264 A | * | 4/1987 | Goudy, Jr. | 210/748 |
| 4,830,757 A | * | 5/1989 | Lynch et al. | 210/742 |
| 5,230,792 A | * | 7/1993 | Sauska et al. | 210/97 |
| 5,547,590 A | * | 8/1996 | Szabo | 210/748 |
| 5,616,457 A | * | 4/1997 | Garc ia-Rubio | 435/4 |
| 5,809,185 A | * | 9/1998 | Mitchell | 385/12 |
| 5,948,272 A | * | 9/1999 | Lemelson | 210/745 |
| 6,235,191 B1 | * | 5/2001 | Nakamura | 210/85 |
| 6,560,543 B2 | * | 5/2003 | Wolfe et al. | 702/22 |
| 6,740,244 B2 | * | 5/2004 | Baca | 210/748 |
| 2001/0049464 A1 | | 12/2001 | Ganz | |
| 2002/0014461 A1 | * | 2/2002 | Kuennen et al. | 210/739 |
| 2002/0049464 A1 | * | 4/2002 | Donofrio et al. | 606/169 |

* cited by examiner

*Primary Examiner*—Frank M. Lawrence

(57) ABSTRACT

A water-borne hazard detection and water treatment system includes sensors (e.g., flow rate, microorganism detectors, and chemical detectors) and can be microprocessor controlled. Microorganisms and/or chemicals are detected within a water distribution system. Treatment areas can be deployed at various stages along a water distribution system. Water entering/passing through a "treatment area" are subjected to light emanating from an ultraviolet laser. UV treated water is provided to its intended point of use after treatment. Filtration can be deployed around input and/or output locations of a system. The system is networkable for communication to remote monitoring agencies (e.g., command and control units) through wired and/or wireless network communications and devices. Networked monitoring and assessment enables rapid deployment of counter measures within affected water distribution systems and populated communities. Emergency distribution shut-off through the distribution network can be based on input from distributed sensors. Multiple treatment systems can be staged.

24 Claims, 3 Drawing Sheets

LASER WATER DETECTION, TREATMENT AND NOTIFICATION SYSTEMS AND METHODS

APPLICATION PRIORITY

This application claims priority to a provisional patent application Ser. No. 60/364,509 filed Mar. 14, 2002 entitled "LASER WATER DETECTION, TREATMENT AND NOTIFICATION SYSTEMS AND METHODS."

BACKGROUND

The water supplied to U.S. communities is potentially vulnerable to terrorist attacks by insertion of biological agents. The possibility of such attacks is now of considerable concern. Biological agents could be a threat if they were inserted at critical points in a water supply system; theoretically, they could cause a large number of casualties.

History repeats itself. Deliberate chemical biological contamination of water supplies has been a common occurrence throughout history. Attacks have ranged from the crude dumping of human and animal cadavers into water supplies to well orchestrated contamination with anthrax and *cholera*. Cyanide has been used as a deadly waterborne poison for thousands of years. In ancient Rome, Nero eliminated his enemies with cherry laurel water (cyanide is the chief toxic ingredient). In the U.S. Civil War, Confederate soldiers shot and left farm animals to rot in ponds during General Sherman's march, compromising the Union water supply. During World War II, the Japanese attacked at least 11 Chinese cities, intending to contaminate food and water supplies with anthrax, cholera, and various other bacteria. Hitler's forces also released sewage into a Bohemia reservoir, deliberately sickening the rival population.

Terrorists are still using chemical or biological weapons (CW/BW). The Aum Shinrikyo Cult attacked a Tokyo subway with sarin gas in 1995 and they are known to have produced and unsuccessfully attempted to use anthrax and botulism toxin nine times as well. In 1985 the Rajneesh religious cult sickened 750 people in The Dalles, Oreg., by spreading *salmonella* bacteria on local salad bars. In an unprecedented violation of the Geneva Conventions, Yugoslav federal forces, or those allied with them, appear to have poisoned wells throughout Kosovo in October/November 1998. Those responsible dumped animal carcasses and hazardous materials (chemicals like paints, oil, and gasoline) into seventy percent of area wells, deliberately sickening the populace and denying them the use of the wells. Since the horrific events of Sep. 11, 2001, Anthrax again surfaced as a threat when a nameless, faceless terrorist used the U.S. Postal Service to deliver biological weapons in the form of letters to senior Government officials and the press.

Despite a history of armies poisoning rival water supplies, institutional dogma has generally downplayed the risk of asymmetric chemical and biological attacks on water. Nationally recognized as critical infrastructures, water systems are vulnerable to disabling attacks. At present, most governments and their relevant agencies lack comprehensive or robust remediation and counter terrorism processes to address this great potential threat.

The nation's water infrastructure is impossible to fully secure. The sheer vastness of the system with its "raw water" reservoirs and tens of thousands of miles of exposed aqueducts and pipeline with little or minimal security, make it logically and fiscally impossible to completely police. The nation's water system is a delicate balance of interlocking components that includes: the water supply system (dams, reservoirs, wells, etc.); water treatment system; and the water distribution system (pipes, pumps storage tanks, etc.). These systems are mostly aging and in urgent need of upgrading, not simply to bolster them from terrorist attack but to keep them adequately handling the growing water needs of the 21st Century.

Raw water is generally treated at the treatment plant to meet federal, state standards, or Department of Defense (for overseas fixed installations) guidelines and to improve its taste and corrosion characteristics. To meet standards, contaminants must be removed or neutralized. Treatment requirements vary greatly depending on raw water quality and community population (these factors affect which standards apply). A small system supplied by a secure well might only require simple chlorination. Larger systems with surface sources have multiple filtration, physical/chemical modification and disinfection units. Common in the U.S., but typically not used in Europe, chlorine disinfectant is added to kill microbial contamination and residual chlorine is maintained to control microbial life within the system. Examples of other chemical addition are precipitation of iron or other metals, reduction of the water's corrositivity and adding fluoride for children. Upon treatment, the water is considered potable or safe to drink.

By its very nature a treatment plant provides both security from and facilitates chemical or biological attack. Treatment processes may very well remove/neutralize an agent introduced into the raw water or local system. On the other hand, it is the controlling point for system quality where chemicals are deliberately and systematically added to the water. The plant lends itself as an ideal attack point for water downstream in the system. Therefore, treatment plants are potential critical points of a water distribution system.

Two particular points in the water system are also of particular vulnerability and could provide harmful effectiveness to terrorists; water intakes and water distribution:

Water intakes: The potential for contamination increases as water dilution decreases, and such is the case for water intakes. There are 6,800 public supply drinking water intakes on rivers alone in the U.S. Likewise; intakes at the mouths of reservoirs or lakes are also vulnerable targets. Contaminates introduced at the intakes have a far better chance of reaching the population than if introduced elsewhere.

Water distribution: This component of the water supply is the most vulnerable. Pipelines wander for thousands of unprotected miles; aqueducts snake through largely unpopulated areas. A person with a crude knowledge of hydraulics and a bicycle tire pump and access to a kitchen faucet could introduce toxins into any local water distribution system, thus endangering thousands. There are few robust security methods in place to protect these distribution systems.

The distribution system is an underground network of iron, concrete or PVC (plastic) pipes that transport the treated water under pressure to the consumers. Ultimately, water is plumbed into each building from these underground mains. High pressure makes it difficult, though not impossible, to inject material into the typically buried lines. A distribution system typically has a variety of valve pits and other control points where maintenance personnel, or an adversary, may gain access to the water.

Though relatively secure, the system pipes and valves are critical points. Any adversary with access to basic chemical, petrochemical, pharmaceutical, biotechnological or related industry can produce biological or chemical (e.g., "biochem") weapons into water supply systems. Compared to aerial attack (inhalation or skin contact), effective doses are easier to obtain in water (less dilution than air and directly ingested by the target), and in many cases the materials are more stable (protected from ultraviolet and temperature extremes, although exposed to chlorine). To effectively kill or disable from drinking water chemical and biological agents must be:

1.—Weaponized, meaning it can be produced and disseminated in large enough quantities to cause desired effect.

2.—A viable water threat, meaning it is infectious or toxic from drinking water.

3.—Stable, meaning the agent maintains its structural and virulent effects in water.

4.—Chlorine resistant, meaning the agent isn't significantly oxidized by free available chlorine (FAC) present in most American water systems. Chlorine susceptibility can be negated by inactivation of system chlorination devices.

There are two types of biological threats, pathogens and toxins. Pathogens are live organisms, such as bacteria, viruses or protozoa, which infect and cause illness and/or death. The other are: biological toxins, chemicals derived from organisms, primarily bacteria and fungi, which cause chemical toxicity resulting in illness and/or death. It is believed that for less than $10,000, anyone with gear no more sophisticated than a home brewing kit, protein cultures and personal protection can cultivate trillions of bacteria with relatively little personal risk.

Mankind wages a constant battle against pathogens. Bacteria, viruses, protozoa, nematodes fungi, and others are the causes of most infectious diseases. Living organisms, they require a host population and certain environmental conditions (temperature, humidity/water, and protection from sunlight) for survival. Upon infection, the pathogen must "grow" in the host. This latency period requires time, depending on the organism, from hours to weeks.

The medical profession, and in particular the dental industry and the medical research community, are taking steps to improve the quality of water used in patient care. Dental unit waterlines (the tubes that connect the high-speed handpiece, air/water syringe and ultrasonic scaler to the water supply) have been shown to harbor a wide variety of microorganisms including bacteria, fungi, and protozoans. These microorganisms colonize and replicate on the interior surfaces of the waterline tubing, inevitably resulting in adherent heterogeneous microbial accumulations termed "biofilms." Biofilms, once formed, serve as a reservoir significantly amplifying the numbers of free-floating microorganisms in water exiting the waterlines. Dental unit water systems currently designed for general dental practice are incapable of efficiently and/or effectively delivering water of an optimal microbiologic quality.

A discussion by Clinical Research Associates (CRA) in its March 1997 newsletter best defines the problem with respect to waterline contamination in the dental field. Water may arrive at a building relatively microbe-free, at about 2 cfu/ml, because of the large diameter water delivery piping. As water lines narrow within the building (within inches in diameter) the microbe count increases to about 10 cfu/ml. At a junction box within the dental unit (with tubing rated at less than an inch in diameter) the count is about 10,000 cfu/ml. After water has traveled about 10 feet within the dental station to the control center, the count can go up to about 400,000 cfu/ml. Finally, at the sterile handpiece and non-sterile air/water supply (the sources of water into a patient's mouth) the microbe count entering the patient's mouth can be 100,000 to 200,000 cfu/ml.

Chemical approaches to disinfecting dental unit water lines have enjoyed varying success. One approach is the use of iodine to disinfect waterlines. The safety and efficacy of chemical disinfection protocols have not been sufficiently validated in the past; therefore the Council has strongly discouraged dentists from treating their dental unit waterlines chemically. In particular, the Council has warned against the use of glutaraldehyde in treatment-water delivery systems to meet the goals set out in the ADA's Statement on Dental Unit Waterlines. Glutaraldehyde is a recognized health hazard; it is a known dermal, mucosal, respiratory and systemic irritant that, as stated on its labeling, is only intended for use in closed containers. In addition to the potentially serious adverse health effects that may be associated with glutaraldehyde when used in dental unit waterlines, such use will essentially fix or "glue" the biofilm matrix to the surface of the waterline, leaving an ideal environment for microbial re-colonization.

To date, however, there is insufficient data to establish the effectiveness of available water sterilization methods. Many of the described methods do not directly address microorganism buildup that may occur within waterlines throughout the day. It is further desirable that treatment in waterlines occur at a point closest to the "point of use" in order to ensure a higher probability of water treatment system effectiveness.

SUMMARY OF THE INVENTION

The present inventors have found that light can be a solution to countering biological and/or chemical ("biochem") terrorism and also propose systems for killing or disabling the harmful effects of some microorganisms. Light at a certain wavelength can excite a catalyst to create hydroxyl radicals, which can sort of perform as bullets for microorganisms. These powerful oxidizing agents break the toughest chemical bonds, and convert biological agents into carbon dioxide and water. The present inventors propose the use of laser-generated radiation (e.g., illumination at certain wavelengths) to kill microorganisms. In accordance with the present invention, a light source illuminating at particular wavelengths into a water treatment area can be effective in killing or disabling harmful microorganisms.

A basic system of the present invention will include a treatment area, which can be presented in the form of a junction box having an entry point for receiving water from input tubing connected to the input portion of the junction box and an exit point for to allow treated water to continue moving towards its point of use. At least one laser light source is coupled to the junction box. The laser light source can be provided in the form of at least one fiber optic line coupled to a laser and also coupled to the junction box, or as at least one laser directly coupled to the junction box, at one or several points about the junction box for delivery of light from laser(s) into the treatment area and onto microorganisms carried by water.

The junction box can comprise of a stainless steel, watertight housing. The internal surfaces of the housing can be highly polished to allow for reflection of light. Reflectors, deflectors and/or diffuser can be included within the housing to scatter light. Baffles or walls can be formed within the housing in order to create flow channels throughout the housing, thereby providing more opportunities for light treatment. The baffles or walls can provide for a serpentine configuration of flow chambers within the housing. Laser light sources can be provided for/within each chamber of the serpentine configuration. When more than one laser is used, each laser can be tuned to (or selected to perform at) a unique wavelength.

A flow sensor can be provided to turn on the laser light source(s) whenever flow through the junction box is sensed. A microorganism detector can be included near the entry point to detect the presence of harmful microorganism. A control means responsive to the detector and/or the flow sensor can turn on the laser light source(s) in response to an indication of either or both flow and/or microorganism detection. Furthermore, a variable wavelength controller can be provided to adjust the wavelength of light produced by laser light source(s). Adjustment to the illumination/wavelength of laser light sources(s) can be in response to said detector, thereby enabling for precise targeting of detected microorganisms.

A filtration capability can be included near or before the entry point of the treatment area. Filtration can reduce or eliminate particles from water prior to laser treatment. Particles can cause light to be absorbed or scattered, thereby reducing the effectiveness of laser treatment, therefore filtration prior to laser treatment is preferred. Filtration can also be provided after treatment, thereby removing additional particulates and/or killed microorganisms.

Treatment systems can be staged as part of a larger system, providing for a system comprising more than one treatment area and associated laser light sources that are coupled, one after the other. Such staging can provide for concentrated redundancy prior to delivery of water to its point of use. Treatment systems can include means to detect and/or analyze microorganisms and/or chemicals within a water distribution system. Detection and/or analysis systems can be deployed at various stages along a water distribution system, near, or as part of, a treatment system, thereby allowing for protection (e.g., detection, treatment) redundancy.

The treatment systems, including detection/analysis means, can be networked to a remote monitoring (e.g., command and control units) through wired and/or wireless networking and communication systems. Networked monitoring and assessment can enable rapid deployment of counter measures within affected water distribution systems and populated communities, to include emergency shut-off of control valves that can be associated with the present systems.

DESCRIPTION OF THE DRAWINGS

The novel features believed characteristic of this invention are set forth in the appended claims. The invention itself, however, as well as a preferred mode of use, further objects, and advantages thereof, will best be understood by reference to the following detailed description of an illustrative embodiment when read in conjunction with the accompanying drawings, wherein:

DETAIL DESCRIPTION OF THE INVENTION

Figure 1:
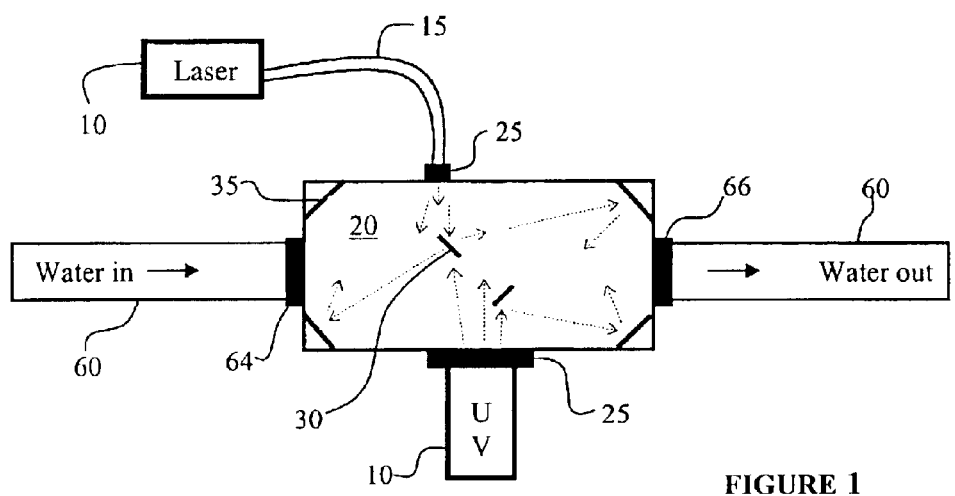
FIG. 1 is as illustration of a laser water treatment system in accordance with one embodiment of the present invention.

The following description is presented to enable persons skilled in the art to make and use the invention, and is provided in the context of particular applications and its requirements. Various modifications to the disclosed embodiments will be readily apparent to those skilled in the art, and the general principles defined herein may be applied to other embodiments and applications without departing from the spirit and scope of the present invention.

Thus, the present invention is not intended to be limited to the embodiments shown, but is to be accorded the widest scope consistent with principles and features disclosed herein. Although preferred embodiments of the present invention are described herein, those skilled in the art can appreciate that a number of varying embodiments may be implemented in accordance with the present invention.

The following U.S. patents and application documents are incorporated herein by reference for their teachings:

U.S. Pat. No. 5,948,272 entitled "SYSTEM AND METHOD FOR DETECTING AND NEUTRALIZING MICROORGANISMS IN A FLUID USING A LASER" and issued to Lemelson on Sep. 7, 1999;

U.S. Pat. No. 5,809,185 entitled "SENSOR FOR DETECTING MICROORGANISMS" and issued to Mitchell on Sep. 15, 1998;

U.S. Patent Application No. 2001/0049464A1 entitled "THERAPEUTIC METHOD AND APPARATUS FOR DEBILITATING OR KILLING MICROORGANISMS WITHIN THE BODY" by Ganz, published Dec. 6, 2001; and U.S. Patent Application No. 2002/0014461A1 entitled "POINT-OF-USE WATER TREATMENT SYSTEM" by Kuennen et al., published Feb. 7, 2002.

Ultraviolet sterilization is one proven method of eliminating a variety of harmful waterborne microorganisms. Short-wave ultraviolet light (e.g., 253.7 nanometers) kills waterborne microorganisms with ease, providing they are exposed to the radiation for a sufficient length of time. The UV light breaks the "DNA chain" thus preventing the microorganism from reproducing. All UV sterilizers are generally provided as a hollow chamber containing an appropriately sized cylindrical UV bulb. Water enters the chamber at the sterilizer inlets, circulates within it for the proper length of time (dwell time) to ensure a high kill rate and returns to the tank via the sterilizer outlet. For maximum benefit, UV sterilizer must generally be run on a continuous 24 hour-per-day basis. UV sterilizers are also highly effective at controlling algae blooms in both marine and freshwater aquaria.

The portion of the UV light spectrum known to affect living organisms ranges in wavelengths from 190 nm to 400 nm and is divided into 3 bands: UVa, UVb, and UVc. The UVc light band of from 100 nm to 280 nm is often referred to as the germicidal band. UVa and UVb light bands are not useful for water sterilization. Many factors, however, affect the overall effectiveness of UV sterilization: the size of the organism may affect the effectiveness of ultraviolet sterilization (the larger the organism the greater the dosage of UVc light required); UV power (the lamp wattage required for sterilization is related to flow rate of water through the UV sterilizer); contact time (determined by the flow rate of the water through the UV sterilizer, very critical); temperature; and the use of quartz sleeves with UV lamps (the amount of UVc output of the UV lamp dependent on the temperature at which it operates.

After the introduction of the ruby laser in 1960, lasers have become widely used in medicine and dentistry for soft tissue surgical procedures and more specifically the CO2 and Nd:YAG lasers for oral soft tissues surgery. Both of these lasers have FDA approval for this function. In the enhancement of a chemical curettage with a laser, the Nd:YAG is ideal because of its use of an optical fiber for the transmittal of the laser energy into the gingival sulcus. Not all lasers are the same. The difference between them is primarily dependent upon their wavelength. Each laser produces light at a different wavelength with a different intensity in a very specific time period. Wavelength affects both the clinical applications and design of the laser. The wavelength of lasers used in medicine and dentistry generally range from 193 to 348 nanometers to 10,600 nanometers.

There are some other characteristics of lasers that need to be understood. A 1064 nanometer wavelength beam from a Nd:YAG laser, for example, will penetrate water to a depth of 60 mm before it is attenuated to 10% of its original strength. Also, the heating effect from a laser will depend greatly on the wattage used and power density at, for example, a fiber optic tip. Furthermore, advances in semiconductor lasers (e.g., VCSELS, vertical cavity surface emitting lasers) should also be considered as a source for the delivery of light at the proper wavelength for treatment purposes in accordance with the present invention.

Referring to FIG. 1, the light source can be provided in the form of a fiber optic cable 15 that extends from a light source 10 to a treatment area 20, so as to carry light from the source 10 through a coupling 25 into the treatment area 20. Light deflectors 30, reflectors 35 or diffusers, e.g., of conical shape, inside the treatment area 20, can be used to spread and/or scatter light rays (shown as dashed arrows) throughout the treatment area 20 so that the light rays can interfere with microorganism contained within water passing through the treatment area 20. Reflector/deflector surfaces to enable effective light scatter are known in the optical arts. Water is carried to the treatment area 20 from a supply line 60. The supply line is coupled to an input port 64 at the treatment area 20. The supply line 60 is again coupled to the treatment area 20 at an exit port 66. It should be appreciated that the treatment area 20 as shown in the drawing can be a self-contained unit that is spliced into an existing water line 60.

The light source 10 can be comprised of any suitable commercially available lighting source useful for emitting light at wavelengths necessary for destroying microorganisms, e.g., a mercury vapor lamp or laser for providing UV radiation. Depending on its environmental application (e.g., constructive limitations of the housing for the treatment area), a laser would preferably be operated intermittently and on low power to the extent the system is enabling the killing or disablement of microorganisms without damaging treatment equipment. But it should be appreciated that lasers or light sources at very high power can also be used depending on the durability of housing materials).

Figure 2:
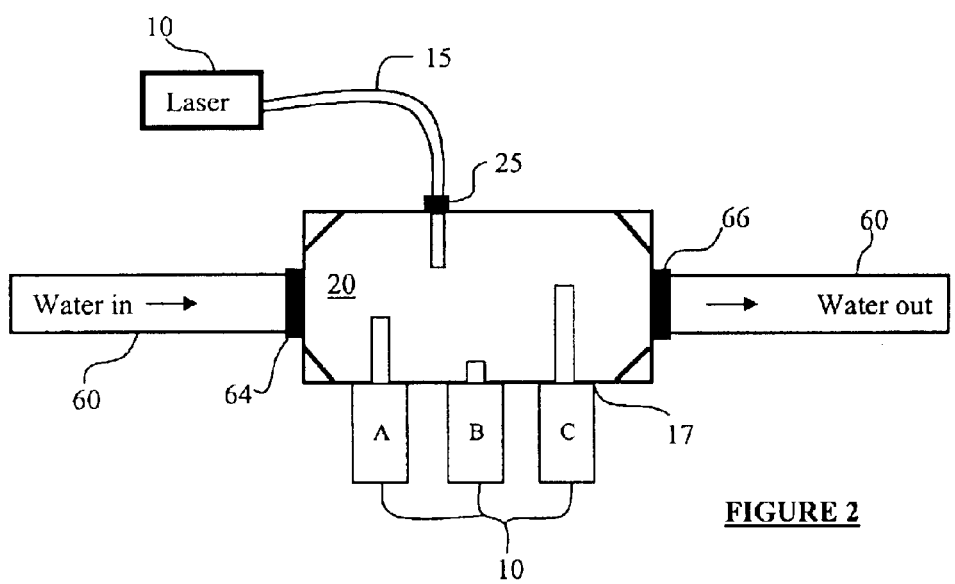
FIG. 2 is an illustration of a laser water treatment system including laser light source depth deployments in accordance with another embodiment of the present invention.

The treatment area and laser configuration can take many forms in order to increase exposure time and laser redundancy. Referring to FIG. 2, a treatment area 20 is shown wherein more than one laser 10 is coupled to the housing of the treatment area 20. Coupling 25 can be directly 17 or by fiber optic 15. Also shown is the placement of laser sources at various depths A, B and C within the treatment area 20. Light sources at various depths within a treatment area will increase exposure and intensity throughout a treatment area. A laser beam is effective to finite depths depending on laser power and water clarity; therefore many light sources at various depths can overcome loss of laser effectiveness due to beam scatter/diffraction within the treatment area 20. Again, optical reflectors, deflectors and/or diffusers can be used in combination with laser source depth to provide effective fluorescence within the treatment area and about the water contained therein.

Figure 3:
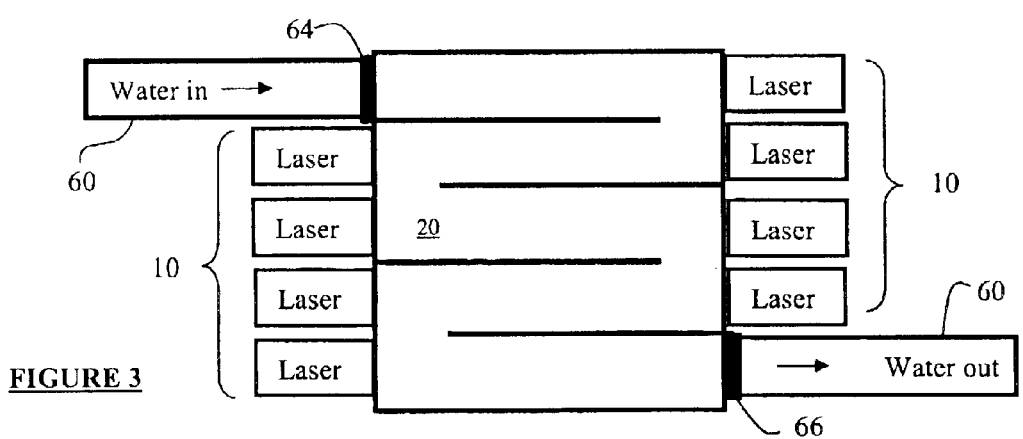
FIG. 3 is as illustration of a laser water treatment system including a serpentinelike configuration in accordance with yet another embodiment of the present invention.

Another proposed treatment area design is provided in a serpentine configuration. As seen in FIG. 3, water entering the treatment area 20 from the waterline 60 at coupling 64 is carried through the treatment area 20 in a serpentine flow pattern because of various partitions built into the treatment area 20. Although four compartments are shown in the illustration, it should be appreciated that more or less compartment can be provided for water flow and light exposure. Furthermore, it should be appreciated that internal surfaces can be rounded, smooth and/or polished in order to promote ease of water flow and maximum light exposure, yet reducing flow restriction. Lasers 10, or fibers, can be coupled to the housing at throughout the various compartments formed by the partitions. The serpentine configuration increases exposure because of the increased number of light sources 10 coupled to the housing and also because of the added length and volume created by the compartments. Exposure time of microorganisms to radiation is generally increased because the serpentine flow pattern creates length to the flow of water.

Figure 4:
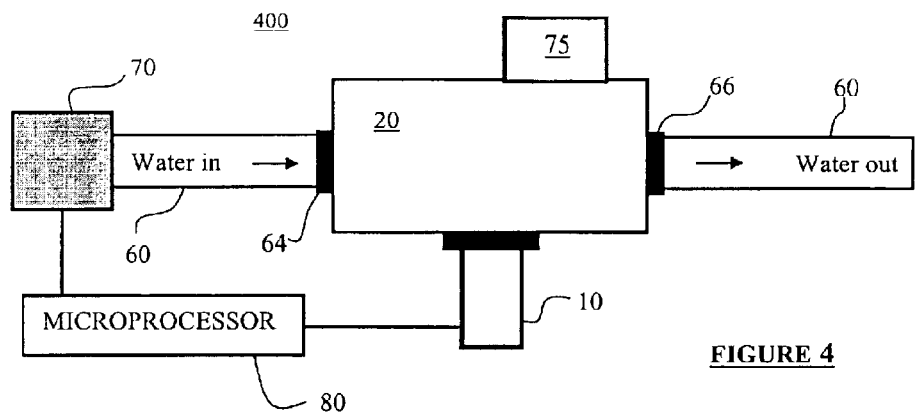
FIG. 4 is an illustration of a laser water detection and treatment system including sensors and a microprocessor in accordance with the present invention.

Referring to FIG. 4, another embodiment of the present invention is illustrated. The system 400 can include a microorganism sensor 70 is deployed near the entry point 64 to the treatment area 20. The sensor 70 can be coupled to a microprocessor 80 (e.g., computer) where sensor input is analyzed to determine if targeted harmful microorganisms exist in water flowing through the pipeline 60. If microorganisms are detected, the microprocessor can control the illumination by light sources 10. The microprocessor can also control the wavelength the light sources illuminate at where it is determined that a particular wavelength of light is most effective against a detected microorganism. The microprocessor can also control more than one light source 10 independently.

A flow sensor 75 can also be provided as part of the system 400 in addition to, or instead of, the microorganism sensor 70. The flow sensor 75 can sense if water is flowing through the treatment area, and in response can turn on the light source(s) 10. It should be appreciated that the flow sensor 75 can be located either at the entry point 64, exit point 66 or within the treatment area 20. Use of the flow sensor 75 will control the amount of time that light sources are turned on. The light sources 10 can turn off when flow is no longer sensed, or after a set time period in which case a timer. Timing can be provided by a microprocessor 80 for each light source 10.

Figure 5:
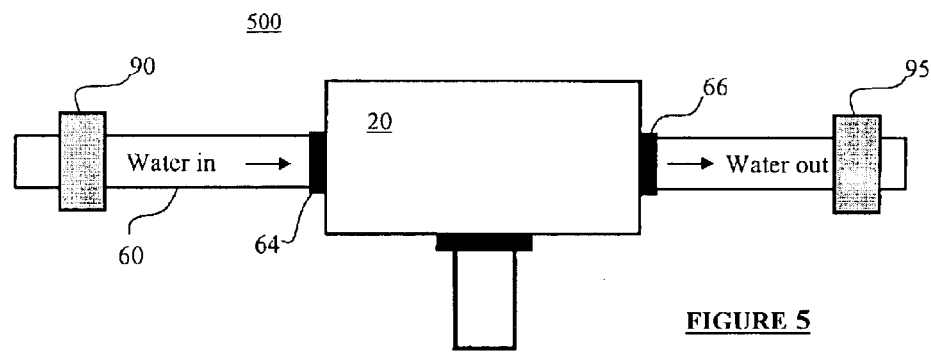
FIG. 5 is as illustration of a laser water treatment system including filtration in accordance with another embodiment of the present invention.

Referring to FIG. 5, a system 500 is shown wherein filtration 90 is incorporated along pipeline 60 before the entry point 64 of the treatment area 20. A filter can remove particles, which would interfere with or absorb the light intended for water treatment. It should be appreciated that a filter 95 could also be provided along pipeline 60 after the treatment area and exit point 66.

Figure 6:
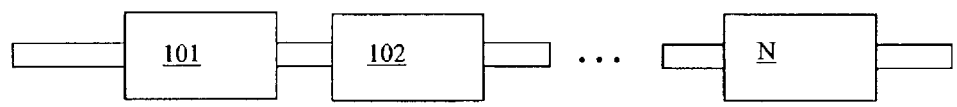
FIG. 6 is an illustration of a laser water detection and treatment system included stages of more than one system in accordance with another embodiment of the present invention.

Referring to FIG. 6, more than one system can be provided in stages in order to maximize treatment success. As shown in FIG. 6, a first treatment system 101 is coupled to a second treatment system 102. Subsequent treatment systems N can be further coupled in line with a prior treatment system. It should be appreciated that each stage (e.g., 101, 102 . . . N) can be tasked to target (e.g., detect and/or impede) the same microorganisms, or can be assigned specific targets and wavelengths.

Figure 7:
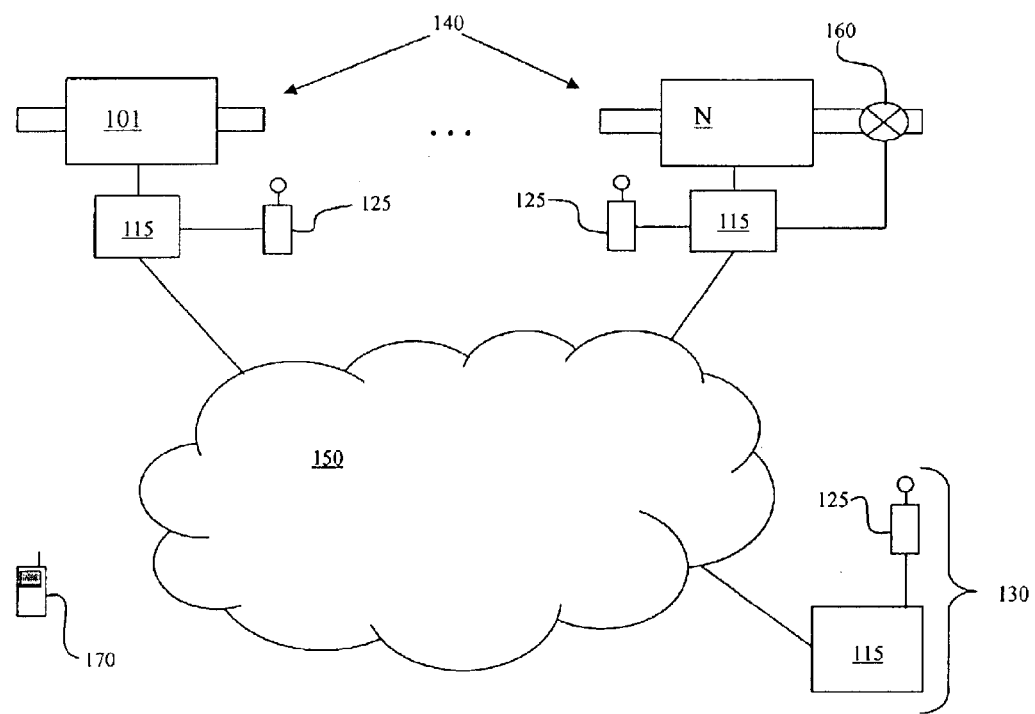
FIG. 7 is an illustration of laser water detection and treatment systems in communication with remote monitoring and control agencies in accordance with another embodiment of the present invention.

Referring to FIG. 7, detection and/or treatment systems 101 can communicate with remote monitoring and control agencies 130 through communication means known in the art. Network 150 communications can be wired and wireless, public and private, secured and unsecured. The field of communications is well developed, therefore it should be appreciated to those skilled in the art that wired 115 and wireless 125 communication equipment can be used to provide at least one of detection, analysis and/or treatment information to remote agencies 130. For example, public wireless network 150 generally communicate using standards and networks such as, among others, 3G, WAP, CDMA, TDMA, GPRS and CPDP. These standards can be used to provide communications between deployed systems (101 through N) at nodes along a water distribution network 140 and responsible monitoring agencies 130 operated by Government and private concerns.

For example, when a biological or chemical agent is detected at system 101, then emergency shut-off procedures can be initiated by the agency 130 to a remote valve 160 that is located safely downstream from the harmful agent. It should be appreciated that monitoring and control can be carried out by a central computing system, thereby providing for automated command and control. It should also be appreciated that a command and control agency 130 can also utilize the assets of a computer to analyze the threat and suggest, or automatically initiate, valve shut-off for several valves deployed throughout the water distribution system (thereby effectively shutting down and isolating the potential threat).

Also, Internet Packet (IP) protocol communication is well known in the data communications art. Therefore, the skilled should appreciate that systems and controllers 130 can communicate status and functions through data networks 150 (e.g., the Internet or private data networks). It should further be appreciated that a hybrid of communications, or communication redundancy, can be provided at each node in an entire system in order to ensure communication is sustained. As broadband communications assets continue to be deployed (e.g., WiFi and Bluetooth communications), it should be appreciated that components within a larger system can communicate status and render command remotely.

Furthermore, it should be appreciated that systems and components deployed throughout water distribution systems can be monitored by personnel in the field using portable wireless devices 170, such as laptops, PDAs (personal digital assistants), Smartphones, and other handheld wireless data-, and network-enabled devices that can be deployed in a field environment.

The embodiments and examples set forth herein are presented in order to best explain the present invention and its practical application and to thereby enable those skilled in the art to make and utilize the invention. However, those skilled in the art will recognize that the foregoing description and examples have been presented for the purpose of illustration and example only. The description as set forth is not intended to be exhaustive or to limit the invention to the precise form disclosed. Many modifications and variations are possible in light of the above teaching without departing from the spirit and scope of the following claims.

We claim:

1. A water-borne hazard detection and water treatment system, comprising:
   detectors deployed at nodes along a water distribution system for detection of biological microorganims or chemicals;
   communications deployed with said detectors at the nodes for reporting detection of the biological microorganisms or chemicals to remote monitoring systems and for receiving treatment commands from said remote monitoring systems; and
   treatment areas deployed at said nodes for providing ultraviolet light into water containing said biological microorganisms or chemicals.

2. The invention of claim 1, further comprising flow sensors deployed at said nodes and ultraviolet laser light sources located within said treatment areas, wherein said sensors turn on the ultraviolet laser light sources whenever fluid flow through said nodes is sensed.

3. The invention of claim 1, further comprising filters deployed at at least one of input or output points relative to said nodes.

4. The invention of claim 1, further comprising at least one shut-off valve deployed at said nodes, said at least one shut-off valve responsive to at least one of said detectors or said remote monitoring systems by blocking water flow through said nodes.

5. The invention of claim 1, said treatment area further comprising a junction box having an entry point for receiving water from input tubing connected to the input portion of the junction box and an exit point to allow treated water to continue moving towards its point of use, and at least one ultraviolet laser light source coupled to the junction box to enable ultraviolet light to illuminate the water when it is located within the junction box.

6. The invention of claim 5 wherein said ultraviolet laser light source can be provided in the form of at least one of: a fiber optic line coupled to a laser and also coupled to the junction box, or as at least one laser directly coupled to the junction box, at at least one point about the junction box.

7. The invention of claim 5 wherein the junction box further comprises a stainless steel, watertight housing wherein internal surfaces of the housing are highly polished to allow for reflection of light.

8. The invention of claim 7 wherein said junction box further comprises at least one of reflectors, deflectors and diffusers within said housing to scatter light provided by said ultraviolet laser light source.

9. The invention of claim 5 further including at least one of baffles or walls that are formed within the housing to create flow channels throughout the housing, wherein said at least one of baffles or walls slow down water flow within said treatment area thereby providing more opportunities for ultraviolet light exposure of water and its treatment.

10. The invention of claim 5 wherein said treatment area includes a housing comprising baffles formed therein, said baffles creating chambers in a serpentine configuration that enable the flow of water through said chambers within the housing.

11. The invention of claim 10 further comprising at least one ultraviolet laser light source assigned to each chamber, wherein each of said ultraviolet laser light source can be tuned to a unique wavelength.

12. A water-borne hazard detection and water treatment system for deployment at nodes along a water distribution system, comprising:

at least one detector, said detector for detecting the presence of biological microorganisms or chemicals in water;

a communication system, said communication system for reporting detection of the biological microorganisms or chemicals by said at least one detector to at least one remote monitoring system and for receiving treatment commands from said at least one remote monitoring system; and a treatment area comprising a housing having an entry point for receiving water into said treatment area and an exit point for to allow treated water to continue moving towards its point of use and at least one ultraviolet laser light source coupled to the housing, said treatment area for providing ultraviolet light into water containing biological microorganisms or chemicals.

13. The invention of claim 12, further comprising at least one shut-off valve responsive to said detector or said at least one remote monitoring system by preventing water flow.

14. The invention of claim 13 wherein said housing is watertight and comprised of stainless steel internal surfaces that are highly polished.

15. The invention of claim 13 wherein said housing further comprises at least one of reflectors, deflectors and diffusers to scatter light provided by said ultraviolet laser light source.

16. The invention of claim 12 said housing further including walls forming channels defining a serpentine configuration wherein water can flow through said channels.

17. A water-borne hazard detection and notification system, comprising:

at least one detector located in nodes deployed along a water distribution system towards water's intended point of use, said detector for detecting the presence of biological microorganisms or chemicals in water flowing towards its intended point of use;

a communication system, said communication system for reporting detection of the biological microorganisms or chemicals by at least one detector deployed in at least one of the nodes to at least one remote monitoring system; and at least one shut-off valve deployed at or near at least one of the nodes, said at least one shut-off valve responsive to at least one of said detectors or said remote monitoring systems by blocking water flow through said nodes.

18. The invention of claim 17 further comprising a treatment area, said treatment area including a housing having an entry point for receiving water into said treatment area and an exit point for to allow treated water to continue moving towards its point of use and at least one ultraviolet laser light source coupled to the housing, said treatment area for providing ultraviolet light into water containing biological microorganisms, wherein treatment is provided within said treatment area in response to treatment commands received from said at least one remote monitoring system through said communication system.

19. The invention of claim 18, wherein said housing is watertight and comprised of stainless steel internal surfaces that are highly polished, includes at least one of reflectors, deflectors and/or diffusers for scattering light provided by said at least one ultraviolet laser light source, and includes walls that form channels which define a serpentine configuration wherein water can flow.

20. The invention of claim 18, further comprising a variable wavelength controller, wherein said at least one ultraviolet laser light source can be adjusted by said variable wavelength controller in response to detection by said detector, thereby enabling for precise targeting of detected microorganisms.

21. The invention of claim 18, further comprising:

a variable wavelength controller provided to adjust the wavelength of light produced by the ultraviolet laser light source in response to detection by said at least one detector.

22. The invention of claim 18, further comprising a flow sensor wherein said flow sensor can cause said at least one ultraviolet laser light source to be turned on whenever water flow through said treatment area is sensed.

23. The invention of claim 18, further comprising at least one filter deployed near at least one of said input or output points.

24. The invention of claim 18, further comprising:

includes a housing comprising baffles formed therein, said baffles creating chambers in a serpentine configuration that enable the flow of water through said chambers within the housing;

at least one ultraviolet laser light source assigned to each of said chambers, wherein each of said ultraviolet laser light source can be tuned to a unique wavelength.

* * * * *